(12) United States Patent
Eastwood et al.

(10) Patent No.: US 7,445,617 B2
(45) Date of Patent: Nov. 4, 2008

(54) TEMPERATURE INDICATING DEVICES AND METHODS OF USE

(75) Inventors: M. Jacqueline Eastwood, Durham, NH (US); N. Joseph Espat, Chicago, IL (US); Michael E. McClurken, Durham, NH (US); Kevin T. Watkins, San Antonio, TX (US)

(73) Assignee: Salient Surgical Technologies, Inc., Dover, NH (US)

( * ) Notice: Subject to any disclaimer, the term of this patent is extended or adjusted under 35 U.S.C. 154(b) by 50 days.

(21) Appl. No.: 10/843,049

(22) Filed: May 10, 2004

(65) Prior Publication Data

US 2005/0250477 A1 Nov. 10, 2005

(51) Int. Cl.
*A61B 18/18* (2006.01)
(52) U.S. Cl. .......................... 606/27; 128/898
(58) Field of Classification Search ............. 606/27–52, 606/1; 128/898
See application file for complete search history.

(56) References Cited

U.S. PATENT DOCUMENTS

| | | | |
|---|---|---|---|
| 3,140,611 A | 7/1964 | Kliewer | |
| 3,682,130 A * | 8/1972 | Jeffers | 116/218 |
| 3,693,579 A | 9/1972 | Kliewer | |
| 3,713,416 A | 1/1973 | Volk | |
| 5,323,730 A | 6/1994 | Ou-Yang | |
| 6,402,742 B1 * | 6/2002 | Blewett et al. | 606/34 |
| 6,603,988 B2 * | 8/2003 | Dowlatshahi | 600/407 |

* cited by examiner

*Primary Examiner*—Michael Peffley
(74) *Attorney, Agent, or Firm*—Grossman, Tucker, Perreault & Pfleger, PLLC

(57) ABSTRACT

A method of treating tissue of a body during a surgical procedure is provided comprising providing tissue comprising normal tissue and abnormal tissue; inserting at least one temperature indicating device into the tissue with the temperature indicating device comprising an indicator to provide an indication of when a trigger temperature has been attained and a trigger mechanism configured to operate when heated to the trigger temperature and trigger the activation of the indicator; heating the tissue sufficiently to ablate at least a portion of the abnormal tissue; and transferring heat from the tissue to the trigger mechanism, the heat sufficient to heat the trigger mechanism to the trigger temperature and trigger the activation of the indicator.

16 Claims, 7 Drawing Sheets

TEMPERATURE INDICATING DEVICES AND METHODS OF USE

FIELD

This invention relates generally to the field of a temperature indicating device for use upon a body. More particularly, the invention relates to a disposable, thermally responsive temperature indicating device for use within tissues of a living human body during surgery, particularly open surgery and minimally invasive surgery such as laparoscopic surgery.

BACKGROUND

Disposable instruments for indicating the internal temperature of food products have been known for some time. One example of such a device is commonly referred to as a "pop-up" temperature indicating device, which includes a cylindrical housing and an indicator rod. The indicator rod is held in a retracted position in the housing by a fusible material, with the retracted position biased by a compressed coil spring. Upon achieving a predetermined temperature, the fusible material softens and looses its hold on the indicator rod. Upon release of the indicator rod from the fusible material, the spring decompresses and moves the indicator rod into an extended position out of the housing.

According to U.S. Pat. No. 5,323,730 entitled "Thermally Responsive Indicator With Organic Retaining Means" to Ou-Yang, the retaining material has typically comprised metal alloys, as in U.S. Pat. Nos. 3,140,611; 3,682,130; 3,693,579 and 3,713,416. The '611 patent, for example, refers to an alloy consisting of bismuth-52%, lead-40%, cadmium-8%, to which is added two parts of Wood's alloy. The '730 Patent goes on to indicate that, while devices employing such alloy retaining materials have proven useful, they have certain drawbacks. For example, such alloys are typically prepared from toxic metallic substances such as bismuth, lead, cadmium and tin.

While disposable temperature indicating devices have been used for indicating the internal temperature of food products, such devices have not been considered for use upon tissues of a living human body during surgery.

Some forms of surgery involve killing tissue to achieve a therapeutic result. The term "ablative surgery" as used herein refers to any of a variety of methods used to kill tissue, with one specific method comprising radio frequency ablation.

To be successful, ablation treatment may require a certain precision. The surgeon must target a particular region, and be careful not to cause unnecessary trauma to surrounding areas of the patient's body near the target area. Just as important, the surgeon must be confident that the procedure within the target area has been appropriately performed. For example, the surgeon may need to determine whether the tissue has been ablated.

What is needed is a disposable temperature indicating device suitable for use upon tissues of a living human body during surgery, particularly during surgery involving ablation.

SUMMARY OF THE INVENTION

According to one embodiment of the present invention, a method of treating tissue of a body during a surgical procedure is provided which comprises: providing tissue comprising normal tissue and abnormal tissue; inserting at least one temperature indicating device into the tissue, with the temperature indicating device comprising an indicator to provide an indication of when a trigger temperature has been attained and a trigger mechanism to trigger an activation of the indicator when heated to the trigger temperature; heating the tissue sufficiently to ablate at least a portion of the abnormal tissue; and transferring heat from the tissue to the trigger mechanism, with the heat sufficient to heat the trigger mechanism to the trigger temperature and trigger the activation of the indicator.

According to another embodiment of the present invention, a method of treating tissue of a body during a surgical procedure is provided which comprises: providing tissue comprising normal tissue and abnormal tissue; inserting at least one temperature indicating device into the tissue, with the temperature indicating device comprising a pop-up temperature indicating device; heating the tissue sufficiently to ablate at least a portion of the abnormal tissue; and transferring heat from the tissue to the pop-up temperature indicating device, with the heat sufficient to trigger the pop-up temperature indicating device.

BRIEF DESCRIPTION OF THE DRAWINGS

To better understand and appreciate the invention, refer to the following detailed description in connection with the accompanying drawings, hand and/or computer generated.

DETAILED DESCRIPTION

Figure 2:
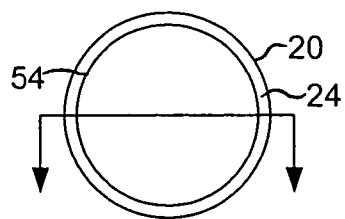
FIG. 2 is a top end view of the temperature indicating device of FIG. 1.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable In other words, features between the various exemplary embodiments described herein are interchangeable as suitable, and not exclusive.

Reference will now be made to the preferred embodiments of the invention, examples of which are illustrated in the accompanying drawings. While the preferred embodiments of the invention describe exemplary temperature indicating devices and methods of use, it should be understood that their combination is for purposes of illustration only. In other words, it should be understood that the use of the temperature indicating devices of the present invention is not limited to the surgical methods disclosed herein. Conversely, it should be equally understood that the methods of the present invention can potentially be used with a wide variety of temperature indicating devices.

An exemplary temperature indicating device 10 according to the present invention is shown throughout FIGS. 1-5. As shown, device 10 preferably comprises a disposable pop-up temperature indicating device. The pop-up temperature indicating device 10 provides a visual indicator to a surgeon, via a two-position, mechanical mechanism, of when a predetermined internal tissue temperature has been achieved upon tissue treatment, without having to measure tissue temperature itself, or monitor temperature gauges over a time period. Furthermore, the temperature indicating device 10 preferably is configured for both open surgery and minimally invasive surgery, such as laparoscopic surgery. For example, for laparoscopic surgery, preferably device 10 is configured to fit through either a 5 mm or 10 mm trocar cannula, and be inserted into tissue at an internal treatment site with reduced trauma to the tissue and patient as compared to open surgery.

The temperature indicating device 10 preferably includes an elongated tubular shaped housing 12 having an intermediate barrel portion 14, a distal (conical) tip portion 16 terminating in a distal pointed tip 18 and a transversely extending ring flange 20 formed opposite the distal pointed tip 18.

Device 10 may be inserted into the tissue of a patient by positioning distal pointed tip 18 against the tissue and pushing the tip 18 manually into the tissue. Device 10 will continue to penetrate through the tissue until the underside surface 22 of flange 20 makes contact with the surface of the tissue.

As shown, preferably the narrowed distal portion 25 of barrel portion 14 includes at least one, and more preferably a plurality (series) of semi-circular tissue engagement protrusions 26 extending at least partially circumferentially around barrel portion 14 and near the distal end of barrel portion 14. Protrusions 26 may be used to better retain the housing 12 in the tissue and inhibit housing 12 from sliding out of tissue when in use.

Apart from protrusions 26, a variety of retention mechanisms may be used with the present invention to help retain the housing 12 in the tissue. However, in order to reduce potential trauma to tissue at the time the device 10 is removed from the patient, preferably the housing 12 does not make use of any retention mechanisms which may result in the tearing of tissue with removal of housing 12 therefrom, such as may occur with, for example, reverse, sharp-tip barbs.

Figure 3:
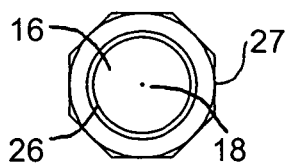
FIG. 3 is a bottom end view of the temperature indicating device of FIG. 1.
Figure 5:
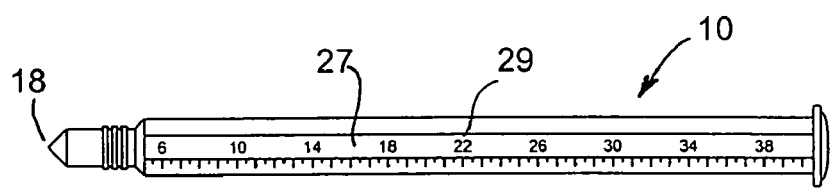
FIG. 5 is a side view of the temperature indicating device of FIG. 1.

Proximal portion 28 of barrel portion 14 may include at least one planar exterior surface 27, as shown in FIGS. 3 and 5, extending longitudinally thereon. More preferably, the proximal portion 28 of barrel portion 14 forms the shape of a polygon as shown in FIG. 3 and, even more preferably, the polygon has an even number of sides such as a hexagon, octagon or decagon.

As shown in FIG. 5, planar surface 27 also preferably includes a series of markings 29 which correspond to the distance from pointed tip 18. In this manner, a length measurement scale is provided which corresponds to the depth of penetration of device 10 into tissue upon insertion. As shown, the length measurement scale comprises numeric reference characters, and is divided into units comprising millimeters with increments from about 6 mm to 40 mm. Other reference characters such as alphanumeric characters may also be used, and other suitable units/increments may comprise, for example, centimeters or inches.

Once in the tissue, the location of device 10 may be located by a surgeon using body imaging techniques including intraoperative ultrasound, computerized tomography (CT) and magnetic resonance imaging (MRI). The planar surface 27 of the proximal portion 28 of barrel portion 14 will generally provide a more detailed ultrasonic image than a curved surface.

Figure 4:
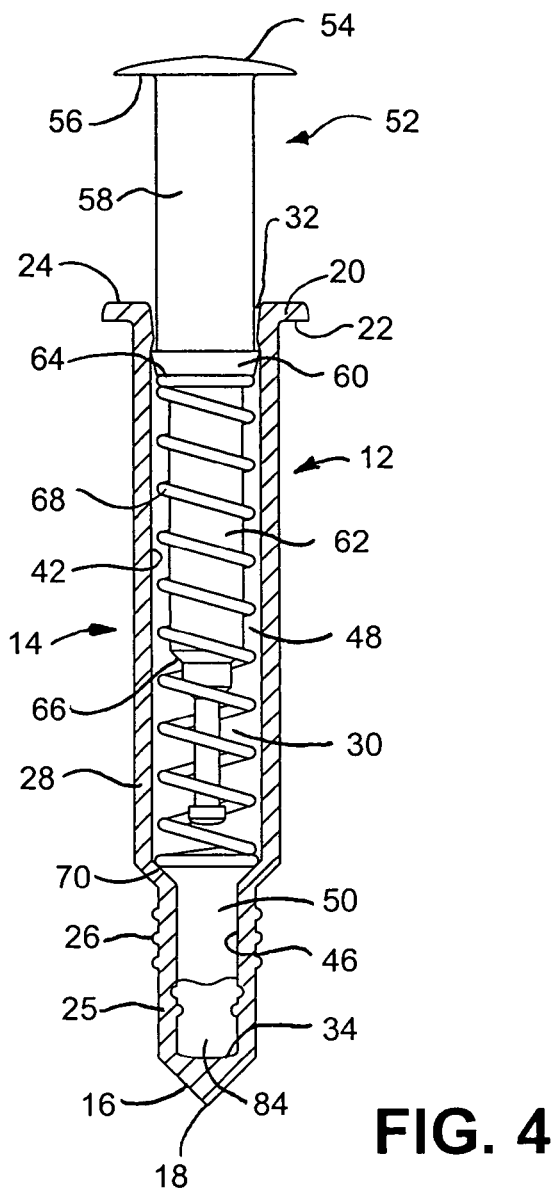
FIG. 4 is a cross-sectional side view of the temperature indicating device of FIG. 1 with the treatment indicator in an extended position.

As best shown in FIG. 4, the housing 12 is preferably formed with a longitudinally extending blind bore 30 extending from an open end 32 in the middle (center) of ring flange 20 to a closed end 34 near tip 18. As shown, the open end 32 preferably has a greater cross sectional opening area than the remainder of bore 30 to help facilitate assembly of temperature indicating device 10 as discussed in greater detail below.

Figure 1:
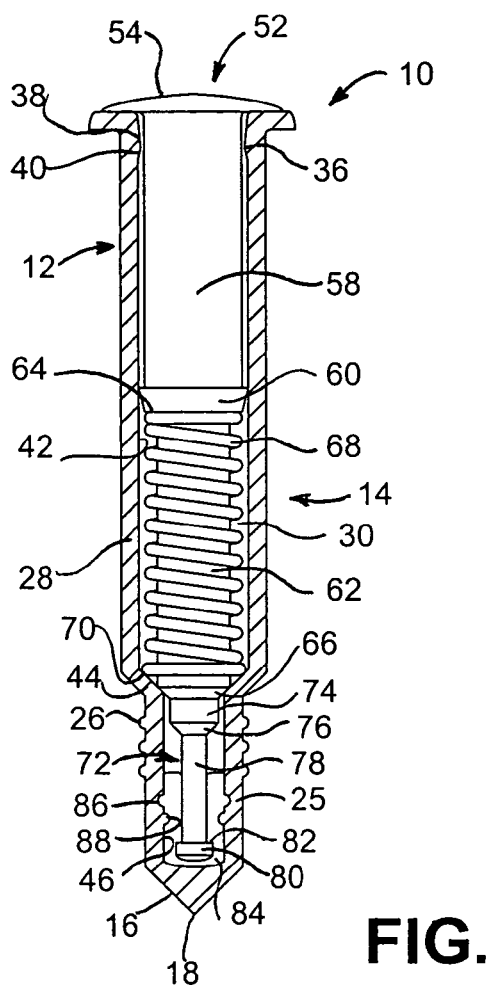
FIG. 1 is a cross-sectional side view of a temperature indicating device according to the present invention with the treatment indicator in a retracted position.

As shown in FIG. 1, and looking into the bore 30 of the housing 12, a localized annular restriction 36 is created in bore 30 by an inward (narrowing) conical tapered portion 38 in barrel portion 14 which initially narrows bore 30 from about the open end 32, and thereafter an outward (widening) conical tapered portion 40 in barrel portion 14 enlarges bore 30. As discussed in greater detail below, the tapered portions 38, 40 defining annular restriction 36 provide both a lead-in for assembly of a treatment indicator rod 52 to housing 12, and thereafter a shoulder which inhibits the removal of indicator rod 52 from the housing 12 once the indicator rod 52 has been assembled thereto.

Spaced inwardly from restriction 36, the bore 30 is made up of a first interior cylindrical portion 42 which extends to inward (narrowing) conical tapered portion 44. Conical tapered portion 44 thereafter extends to second interior cylindrical portion 46 which terminates in closed end 34. In accordance with bore 30, the interior cavity of housing 12 comprises a first cylindrical cavity 48 and a second cylindrical cavity 50.

As shown in FIG. 1, the cylindrical portion 46 of housing 12 may include at least one outward (widening) recess 86, and at least one inward (narrowing) protrusion 88 into cavity 50. Here, recess 86 comprises a semi-circular recess extending at least partially circumferentially around interior cylindrical portion 46, while protrusion 88 comprises a semi-circular protrusion extending at least partially circumferentially around interior cylindrical portion 46.

As shown in FIGS. 1 and 4, an indicator rod 52 is positioned in the bore 30 of housing 12. In FIG. 1 the indicator rod 52 is shown in a retracted untriggered (unfired) position relative to the housing 12 while in FIG. 4 the indictor rod 52 is shown in an extended triggered (fired) position relative to the housing 12. During use of device 10, the indictor rod 52 slides between the retracted and extended positions as discussed in greater detail below.

The indicator rod 52 preferably includes an enlarged cap portion 54 which completely covers the open end 32 of bore 30. Furthermore, the planar underside surface 56 of the cap portion 54 is preferably configured to mate with the planar upper surface 24 of the flange 20 on the housing 12. In the above manner, the device 10 is configured to inhibit fluids present during surgery from entering the housing 12.

At the upper or proximal end of the indicator rod 52 beneath the enlarged cap portion 54 is located a rod head portion 58 which extends to a collar portion 60. As shown, the rod head portion 58 preferably has a diameter smaller than the diameter of annular restriction 36 such that rod head portion 58 may slide within annular restriction 36.

Preferably the diameter of rod head portion 58 is only slightly smaller than the diameter of annular restriction 36 (about 0.025 mm-0.1 mm) as to inhibit fluids present during surgery from entering the housing 12 between the rod head portion 58 and annular restriction 36. Furthermore, with this configuration annular restriction 36 is also configured to guide the sliding of rod 52 within bore 30.

As shown, collar portion 60 preferably has a diameter smaller than the diameter of cylindrical portion 42 such that collar portion 60 may slide within cylindrical portion 42, but greater than the diameter of annular restriction 36 to inhibit the removal of indicator rod 52 from the housing 12 once the indicator rod 52 has been assembled thereto. To assemble rod 52 to housing 12, collar portion 60 may be forced into cavity 48 past annular restriction 36 at a high rate of speed possibly while the housing 12 is simultaneously heated to soften and/or expand.

Preferably the diameter of collar portion 60 is only slightly smaller than the diameter of cylindrical portion 42 (about 0.025 mm-0.1 mm) as to inhibit fluids present during surgery from entering cavities 48 and 50 of the housing 12 between the collar portion 60 and cylindrical portion 42. Furthermore, preferably the collar portion 60 is configured to seat against the annular restriction 36 (when the indicator rod 52 is in its extended position) to also inhibit fluids present during surgery from entering cavities 48 and 50 of the housing 12 between the collar portion 60 and annular restriction 36. To provide a better seal, o-rings may also be used in a manner known in the art.

Beneath the collar portion 60 is located an indicator rod intermediate portion 62 which extends to a conical tapered portion 66. As shown, preferably intermediate portion 62 has a diameter smaller than that of collar portion 62 such that a linear coiled spring 68 overlying intermediate portion 62 may seat against and be compressed against the collar shoulder 64. Furthermore, in this manner, intermediate portion 62 provides a mandrel to support the interior of spring 68.

As shown in FIG. 1, conical tapered portion 66 is configured to seat against conical tapered portion 44 of housing 12 to inhibit fluids present during surgery from entering cavity 50 of the housing 12 between conical tapered portion 66 of rod 52 and conical tapered portion 44 of housing 12.

As shown, conical tapered portion 44 of housing 12 also provides an opposing shoulder portion 70 for seating spring 68 there against. In this manner, spring 68 may now be compressed between the collar shoulder 64 of the indicating rod 52 and slanted shoulder 70 of the housing when the indicator rod 52 is fully inserted in the housing 12.

Beneath tapered portion 66 of rod 52, a rod distal portion 72 comprises cylindrical portion 74 which thereafter extends to conical tapered portion 76 and cylindrical portion 78 with the rod terminating in expanded distal tip portion 80. As shown, preferably the rod distal portion 72 has a diameter smaller than the diameter of cylindrical portion 46 of housing 12 such that rod distal portion 72 may enter cylindrical cavity 50.

Conical tapered portion 76 provides a lead-in for cylindrical portion 74 into cylindrical cavity 50. Cylindrical portion 74 preferably has a diameter only slightly smaller than the diameter of cylindrical portion 46 to promote the centering of cylindrical portion 78 and expanded distal tip portion 80 within cavity 50.

A fusible material 84 at least partially fills cavity 50 around the distal portion 72 of rod 52. The fusible material 84 is preferably in the form of a solid under normal room temperature conditions, about 22° C. (degrees Celsius), as shown in FIG. 1.

As also shown in FIG. 1, cylindrical portion 78 is partially embedded in fusible material 84 and expanded distal tip portion 80 is completely embedded in fusible material 84 to retain the indicator rod 52 in the housing 12. Increasing or decreasing the amount of fusible material 84 may be used to respectively increase or decrease both the surface area of the cylindrical portion 78 of rod 52 and cylindrical portion 46 of housing 12 engaged by the fusible material 84, and hence increase or decrease the retention strength of the indicator rod 52 to the housing 12 by fusible material 84.

As shown in FIG. 1, when fusible material 84 is a solid, a mechanical engagement between the fusible material 84 and rod 52 is created by the fusible material 84 overlying shoulder 82 of expanded distal tip portion 80. Similarly, mechanical engagement between the fusible material 84 and housing 12 is created by the fusible material 84 within recess 86 and the fusible material 84 underlying protrusion 88. These various mechanical engagements further increase the retention strength of the indicator rod 52 to the housing 12 by fusible material 84.

The fusible structural link between indicator rod 52 and housing 12 provided by material 84 is configured to physically weaken (e.g. by softening and/or melting into a liquid) and deform, and lose its ability to retain indicator rod 52 at its retracted position against the force of spring 68 at a predetermined trigger temperature, thus providing a trigger mechanism for the release of indicator rod 52. Thereafter, the decompression force associated with compressed spring 68 provides a propulsion mechanism for the travel of indicator rod 52 from its retracted to extended positions.

Preferably the fusible material 84 has a melting temperature or softening temperate in the range between and including about 45° C. to 80° C. (113° F. to 176° F.), and more preferably in the range between and including about 50° C. to 75° C. (122° F. to 167° F.), and even more preferably in the range between and including about 55° C. to 70° C. (131° F. to 158° F.). As discussed in greater detail below, the fusible material is heated with heat which has transferred from the tissue to device 10.

Fusible material 84 may comprise various materials, including metals, metal alloys, polymers and organic materials. However, preferably fusible material 84 comprises a material biocompatible with the human body. As used herein, a "biocompatible material" refers to a material having the properties of not producing toxic or injurious effects on biological function, and not provoking a significant rejection or immune response. Preferably, the material as used complies with international standard ISO 10993 (International Standards Organization) for biological evaluation of medical devices. An exemplary fusible material comprises wax, and more preferably sterile beeswax.

Figure 6:
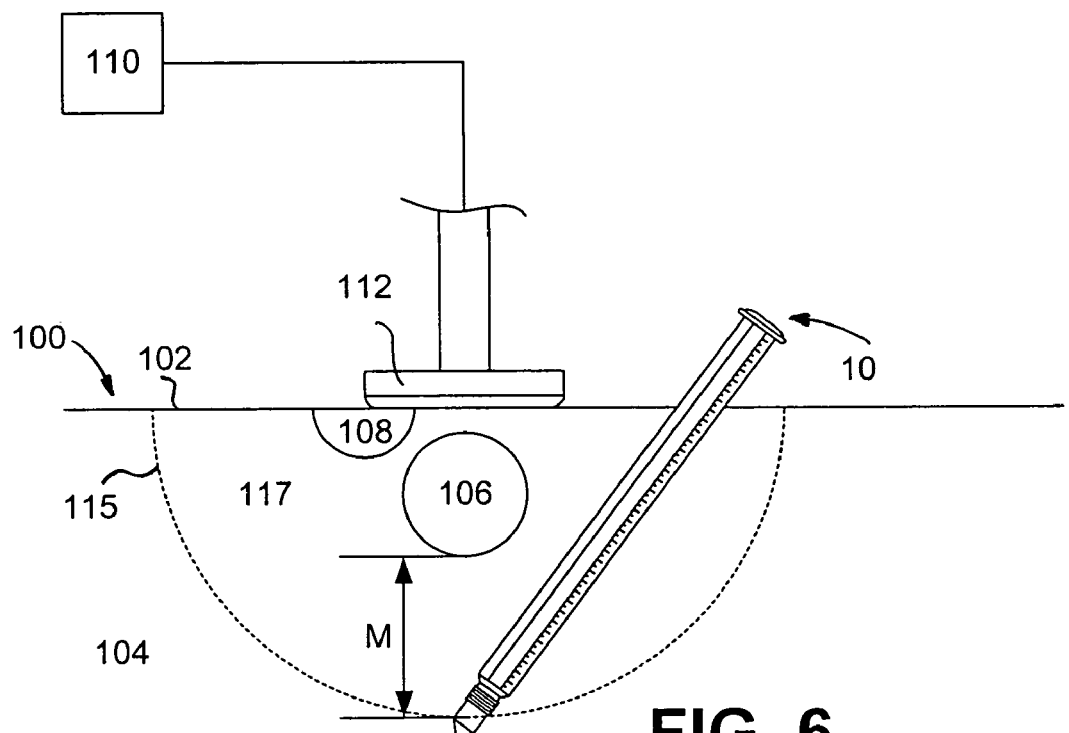
FIG. 6 is a side view of the temperature indicating device of FIG. 1 inserted into tissue and used with a body imaging device.

An exemplary medical use for the temperature indicating device 10 disclosed herein involves the treatment of at least one mass of abnormal tissue (e.g. tumor, neoplasm, cyst) at least partially surrounded by normal (healthy) tissue. As shown in FIG. 6, tissue 100 comprises normal tissue 104, as well as abnormal tissue 106 and 108. As shown, abnormal tissue 106 comprises a tumor and, more specifically, a completely "sub-surface" tumor. In other words, a tumor which is located completely beneath the tissue surface 102. Alternatively, abnormal tissue 108 comprises a "surface" tumor where at least a portion of the tumor is present at the tissue surface 102.

As shown in FIG. 6, in order to locate the boundaries of abnormal tissue 106 and 108, a surgeon preferably will first use a body imaging apparatus 110 in a known manner. Body imaging apparatus 110 preferably comprises an ultrasonic body imaging apparatus. However, other body imaging methodologies and apparatus may be used, including computerized tomography (CT), magnetic resonance imaging (MRI) and X-ray.

Figure 7:
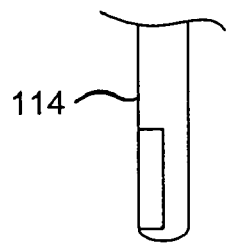
FIG. 7 is a side view of an alternative imaging probe for use with the body imaging device of FIG. 6.

As shown, body imaging apparatus 110 makes use of a disc-shaped imaging probe 112 configured for open surgery. However, imaging probe 112 may also be configured for laparoscopic surgery and passage through a trocar cannula, such as the cylindrical imaging probe 114 shown in FIG. 7.

Once the surgeon has located and positioned the abnormal tissue 106, 108 through the use of the body imaging apparatus 110, the surgeon may then insert temperature indicating device 10 into the tissue 100. As indicated above, temperature indicating device 10 may be inserted into the tissue 100 of a patient by positioning distal pointed tip 18 against the tissue 100 and pushing the tip 18 into the tissue 100. As shown in FIG. 6, temperature indicating device 10 has been inserted into tissue 100 at an angle of about 30-60° (e.g.,forty-five degrees) normal to the tissue surface 102.

Before inserting temperature indicating device 10 into tissue 100, preferably the surgeon has identified a targeted tissue treatment section 117 with a border 115 which includes a predetermined margin M of normal tissue 104 around abnormal tissue 106, 108. From predetermined margin M of normal tissue 104, preferably the surgeon will then insert the temperature indicating device 10 into tissue 104 as to position the thermally responsive fusible material portion of temperature indicating device 10 at the border 115 of the predetermined margin M and targeted tissue treatment section 117. In this manner, the surgeon will be alerted by the triggering of temperature indicating device 10 once the tissue 104 at the border 115 has been treated as desired, and the treatment of tissue 104, 106 and 108 within the targeted tissue treatment section 117 should be considered complete.

As shown in FIG. 6, preferably the surgeon will insert temperature indicating device 10 only into normal tissue 104 as to inhibit any spread of abnormal tissue 106, 108. The size of the predetermined margin M depends on numerous factors including whether the abnormal tissue 106, 108 is capsulized. If the abnormal tissue 106, 108 is capsulized, the predetermined margin may be somewhat smaller than if the abnormal tissue 106, 108 is uncapsulized.

Figure 8:
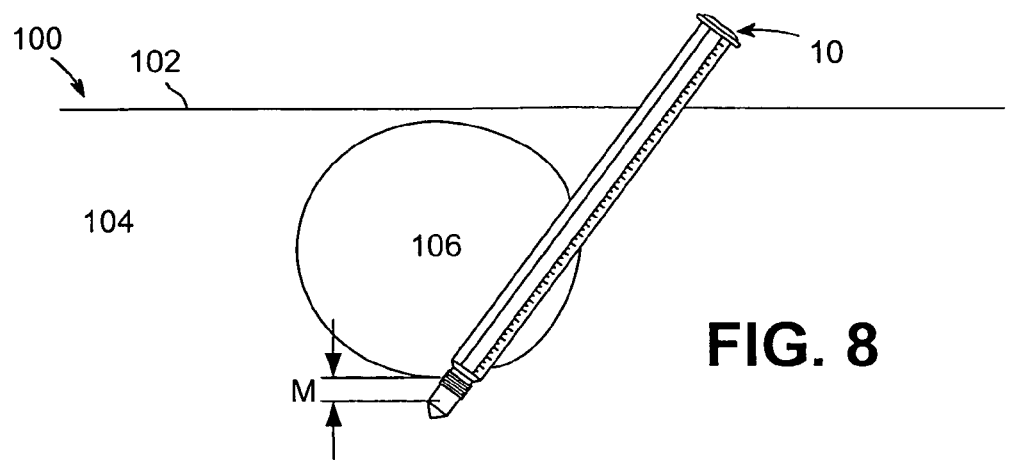
FIG. 8 is a side view of another embodiment of inserting the temperature indicating device of FIG. 1 into tissue.

In certain instances it is recognized that temperature indicating device 10 may have to be partially inserted into abnormal tissue 106, such as shown in FIG. 8, where the mass of abnormal tissue 106 is particularly large. In this situation, it may be desirable to have the thermally responsive fusible material portion of temperature indicating device 10 penetrate through the abnormal tissue 106 and be located in normal tissue 104 to provide predetermined margin M.

Figure 9:
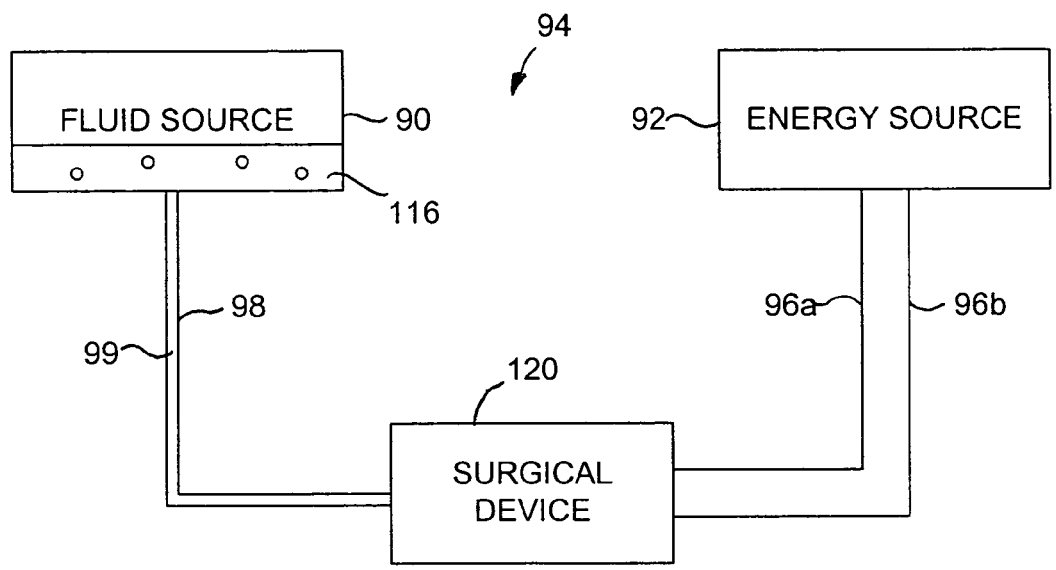
FIG. 9 is a block diagram of an electrosurgical system used with the temperature indicating device of FIG. 1.

After temperature indicating device 10 has been inserted into normal tissue 104, the tissue 100 is then preferably treated with a hand held and manipulated surgical device configured to provide energy to the tissue 100 to heat the tissue 100. An exemplary system 94 having a surgical device 120 is shown in FIG. 9. Surgical device 120 preferably comprises an electrosurgical device and more preferably comprises a bipolar, radio frequency, electrosurgical device. Even more preferably, surgical device 120 comprises a fluid-assisted, bipolar, radio frequency, electrosurgical device. Such devices assigned to the assignee of the present invention are disclosed in PCT International Publication Nos. WO 03/024349 A1 and WO 03/082134 A1, both entitled "Fluid-Assisted Medical Devices, Systems and Methods" and hereby incorporated by reference in their entirety.

As shown in FIG. 9, electrosurgical device 120 is preferably part of a system 94 comprising a fluid source 90 and an electrical energy source 92. Electrosurgical device 120 is preferably coupled to energy source 92 via insulated wire conductors 96a, 96b. With respect to the fluid coupling, fluid 116 from the fluid source 90 is preferably communicated from fluid source 90 to electrosurgical device 120 through a flexible, polyvinylchloride (PVC) fluid line 98 having a lumen 99.

Energy source 92 preferably comprises a generator, and more preferably a radio frequency alternating current generator which may provide radio frequency power therefrom at selected increments. Fluid source 90 preferably comprises an intravenous bag containing electrically conductive fluid, which more preferably comprises saline. More preferably, the saline comprises sterile, and even more preferably, normal saline. Although the description herein will specifically describe the use of saline as the fluid, other electrically conductive fluids, as well as non-conductive fluids, can be used in accordance with the invention.

For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

Figure 10:
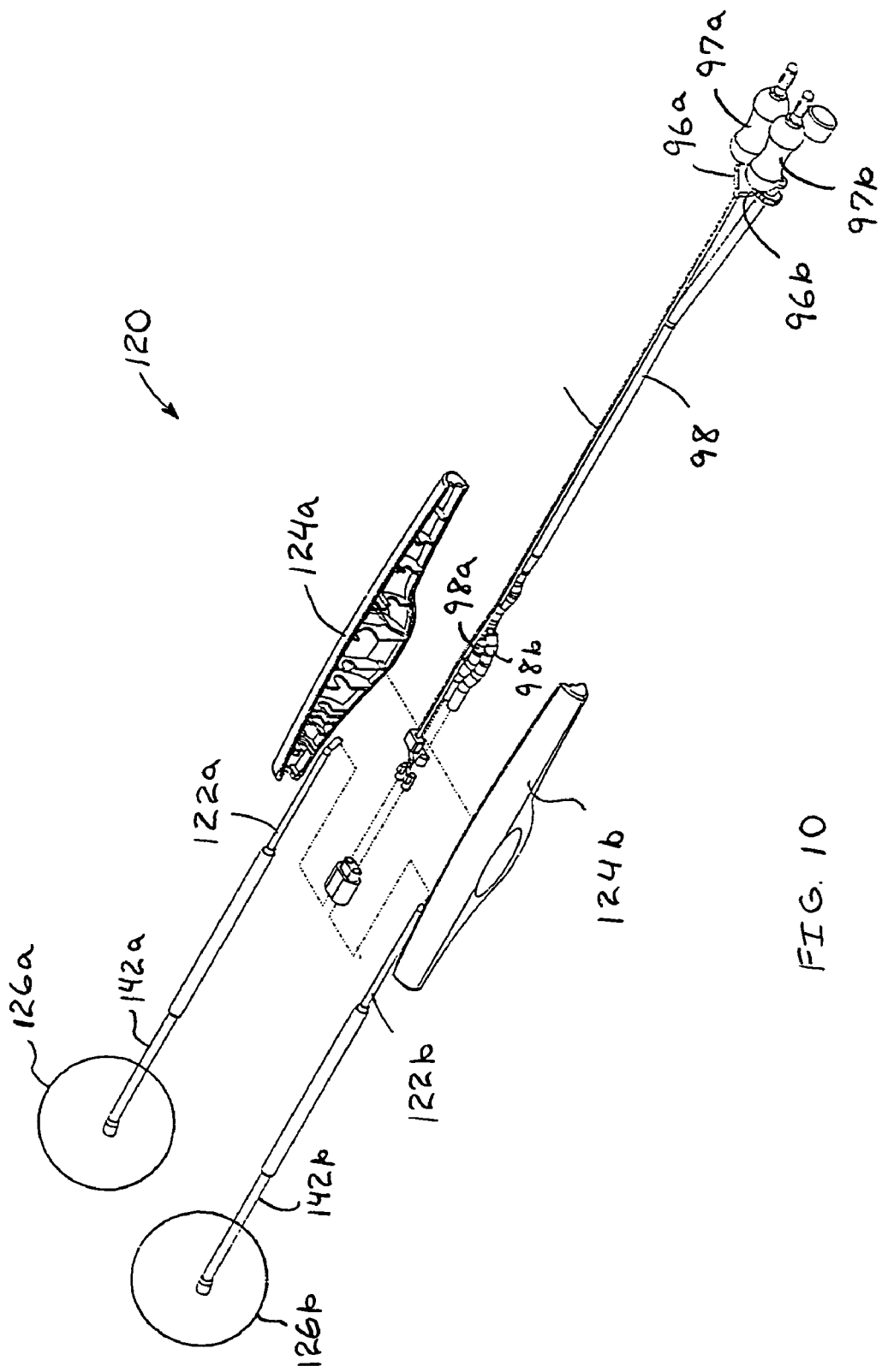
FIG. 10 is an exploded perspective view of an assembly of an electrosurgical device used with the temperature indicating device of FIG. 1
Figure 11:
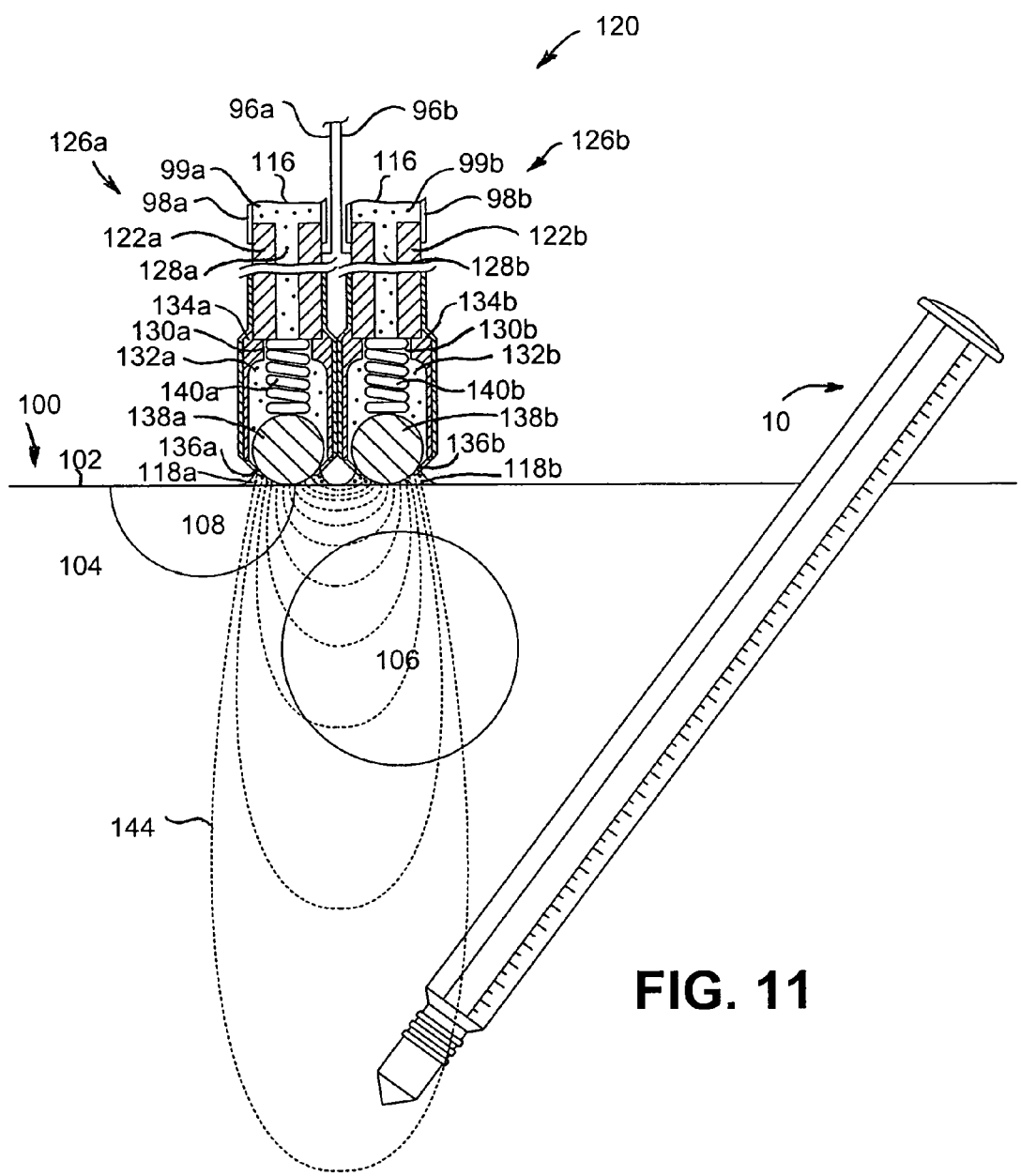
FIG. 11 is a cross-sectional side view of a distal end portion of the electrosurgical device of FIG. 10 in conjunction with the temperature indicating device of FIG. 1 in tissue.

An exemplary electrosurgical device 120 configured to provide radio frequency power and fluid simultaneously during the treatment of tissue 100, and which may be used in conjunction with the system and methods of the present invention, is shown in FIGS. 10 and 11. As shown electrosurgical device 120 comprises a bipolar electrosurigcal device. With a bipolar device, in the presence of alternating current, an electrical circuit is created with the electrodes of the device, which alternate in polarity between positive and negative charges with the current flow from the positive to the negative charge.

As shown in FIG. 10, bipolar electrosurgical device 120 preferably includes two arms comprising rigid, self-supporting, hollow shafts 122a, 122b, a proximal handle comprising mating handle portions 124a, 124b and arm tip portions as shown by circles 126a, 126b. In this embodiment, shafts 122a, 122b preferably comprise thick walled metal hypotubing. In this manner, the shafts 122a, 122b have sufficient rigidity to maintain their form during use of device 120 without kinking or significant bending. The handle is configured for hand holding of device 120, and for hand manipulation of tip portions 126a, 126b of device 120. It is preferably made of a sterilizable, rigid, non-conductive material, such as a polymer (e.g., polycarbonate).

As shown in FIGS. 9, fluid 116 for device 120 is first communicated down lumen 99 of fluid line 98. As shown in FIGS. 10 and 11, fluid 116 then flows from lumen 99 of fluid line 98 to lumens 99a, 99b of fluid lines 98a, 98b. Fluid lines 98a, 98b are preferably interference fit over the outside diameter of shafts 122a, 122b to provide a press fit seal there between. As shown in FIG. 11, fluid 116 then flows within the lumens 128a, 128b of shafts 122a, 122b and through the lumens 130a, 130b and cavities 132a, 132b of metal sleeves 134a, 134b disposed at the end of shafts 122a, 122b where it is expelled from outlet openings 136a, 136b around the electrodes 138a, 138b, which comprise solid metal balls. Electrodes 138a, 138b are retained within sleeves 134a, 134b by crimps located at the distal end of the sleeves 138a, 138b.

Radio frequency energy for electrodes 138a, 138b is provided from electrical energy source 92 through insulated wire conductors 96a, 96b which are electrically coupled (e.g. welded) to shafts 122a, 122b and connectable to energy source 92 via two banana (male) plug connectors 97a, 97b. Electric current from energy source 92 thereafter flows from shafts 122a, 122b to metal sleeves 134a, 134b, springs 140a, 140b and finally to electrodes 138a, 138b which are all in physical contact. Electrical insulators 142a, 142b, preferably comprising shrink wrap polymer tubing, surround shafts 122a, 122b and sleeves 134a, 134b along substantially their entire exposed length.

As best shown in FIG. 11, when device 120 is in use electrodes 138a, 138b are laterally spaced adjacent tissue surface 102 of tissue 100. As shown, the electrodes 138a, 138b are fluidly coupled to the surface 102 of tissue 100 by fluid couplings 118a, 118b which preferably comprise discrete, localized webs and more specifically comprise triangular shaped web portions which provide a film of fluid 116 between surface 102 of tissue 100 and electrodes 138a, 138b. When the user of electrosurgical device 120 places electrodes 138a, 138b at a tissue treatment site and moves electrodes 138a, 138b across surface 102 of tissue 100, fluid 116 is expelled around and on the surfaces of electrodes 138a, 138b at the distal ends of sleeves 134a, 134b and onto surface 102 of tissue 100 via couplings 118a, 118b. At the same time, radio frequency electrical energy (current), shown by electrical field lines 144, is provided to tissue 100 at tissue surface 102 and below tissue surface 102 into tissue 100 through fluid couplings 118a, 118b.

In addition to fluid 116 providing an electrical coupling between the electrosurgical device 120 and tissue 100, fluid 116 lubricates surface 102 of tissue 100 and facilitates the movement of electrodes 138a, 138b across surface 102 of tissue 100. During movement of electrodes 138a, 138b, electrodes 138a, 138b typically slide across the surface 102 of tissue 100, but also may rotate as electrodes 138a, 138b move across surface 102 of the tissue 100. Typically the user of electrosurgical device 120 slides electrodes 138a, 138b across surface 102 of tissue 100 back and forth with a painting motion, preferably in an outwardly spirally circular pattern over the abnormal tissue 106, 108 while using fluid 116 as, among other things, a lubricating coating. Preferably the thickness of the fluid 116 between the distal end surface of electrodes 138a, 138b and surface 102 of tissue 100 at the outer edge of couplings 118a, 118b is in the range between and including about 0.05 mm to 1.5 mm. More preferably, fluid 116 between the distal end surface of electrodes 138a, 138b and surface 102 of tissue 100 at the outer edge of coupling 118a, 118b is in the range between and including about 0.1 mm to 0.3 mm. In certain embodiments, the distal end tip of electrodes 138a, 138b may contact surface 102 of tissue 100 without any fluid 116 in between.

With use of electrosurgical device 120, the heating of the tissue 100 is generated due to the electrical resistance of the tissue 100. In other words, increasing the temperature of the tissue 100 as a result of electric current flow through the tissue 100, with the electrical energy being absorbed from the voltage and transformed into thermal energy (i.e. heat) via accelerated movement of ions as a function of the tissue's electrical resistance. In addition to the heating of tissue 100, thermal heat generated in tissue 100 is transferred to device 10 and thereafter to fusible material 84.

Deleterious effects in the cells making up the tissue 100 begin to occur at about 42° C. As the temperature of the tissue 100 increases due to heat generated by the tissue's resistance, the tissue 100 will undergo profound changes and eventually, as the temperature becomes high enough, that is, generally greater than 45° C., the cells will die. As the temperature increases beyond cell death temperature, complete disintegration of the cell walls and cells may be caused by boiling of the tissue's (intracellular and intercellular) water. Cell death temperatures can vary with the type of tissue to which the power is being applied, but generally will begin to occur within the range of about 45° C. to 60° C., though actual cell death of certain tissue cells may occur at a higher temperature.

Figure 12:
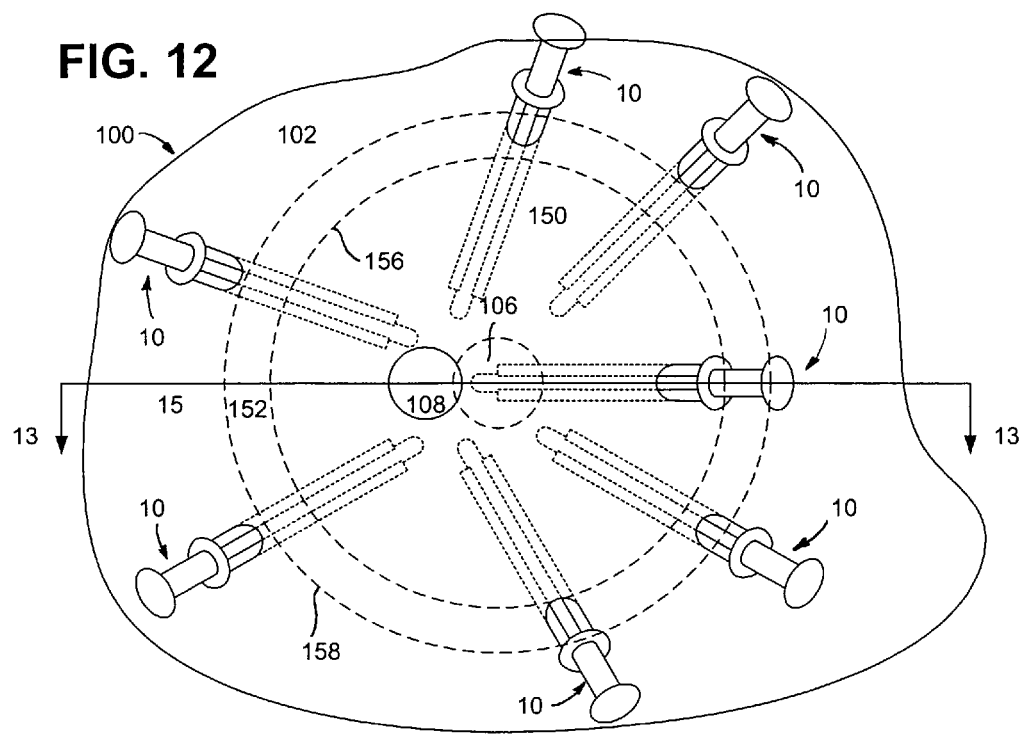
FIG. 12 is a top (plan) view of the tissue after being treated with the electrosurgical device of FIG. 10.
Figure 13:
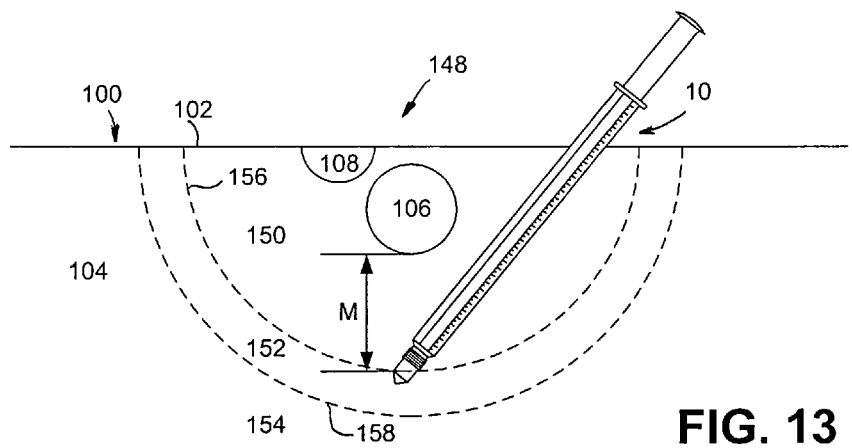
FIG. 13 is a cross-sectional side view of the tissue of FIG. 12 taken along section line 13-13 of FIG. 12.

FIGS. 12 and 13 show tissue 100 after it has been treated with use of electrostirgical device 120. FIG. 12 shows a top view of the tissue 100, which also shows a plurality of temperature indicating devices 10 arranged so as to surround abnormal tissue 106, 108.

FIG. 13 shows a cross-section of the tissue treated with use of electrosurgical device 120 taken along line 13-13 of FIG. 12. More specifically, FIG. 13 shows a cross-sectional side view of a semi-spherical treated tissue section 148 which is defined by border 158. Treatment section 148 may be subdivided into an ablation zone 150 and a hemorrhagic zone 152. In addition to border 158 defining the tissue treatment section 148, border 158 also defines the outer border of hemorrhagic zone 152. The transition between ablation zone 150 and a hemorrhagic zone 152 is defined by border 156.

Ablation zone 150 comprises tissue which has been thermally heated during the surgical procedure sufficiently to kill the cells thereof, while hemorrhagic zone 152 comprises tissue which has been thermally heated during the surgical procedure, but not sufficiently to kill the cells thereof. Native zone 154 comprises tissue unaltered by the surgical procedure.

As shown in FIGS. 12 and 13, it is important that the ablation zone 150 at least encompass the detected abnormal tissue 106 and 108. Furthermore, as shown in FIG. 13, preferably ablation zone 150 typically includes at least a portion, and more preferably all, of the predetermined margin M of normal tissue 104 around the abnormal tissue 106, 108 to better ensure that all the abnormal tissue 106, 108 is within ablation zone 150.

While obtaining a predetermined margin M of normal tissue 104 ablation may be preferred, minimizing the amount of normal tissue 104 ablation outside the margin M is also desirable. By positioning the thermally responsive fusible material portion of temperature indicating device 10 at the border 115 of the predetermined margin M and targeted tissue treatment section 117 (as shown in FIG. 6), the surgeon is assured that the ablation zone 150 substantially coincides with the targeted tissue treatment section 117. In this manner, no more normal tissue 104 is ablated than desired.

While the use of a margin M has been described with respect to the use of one of the temperature indicating devices 10 shown in FIG. 12, it should be understood that all the temperature indicating devices 10 shown in FIG. 12 preferably make use of a margin M. It should also be understood that the exact shape of the treated tissue section 148 depends on the shape of the abnormal tissue 106, 108 and that a spherical treated tissue section 148 as described herein is merely exemplary.

Figure 14:
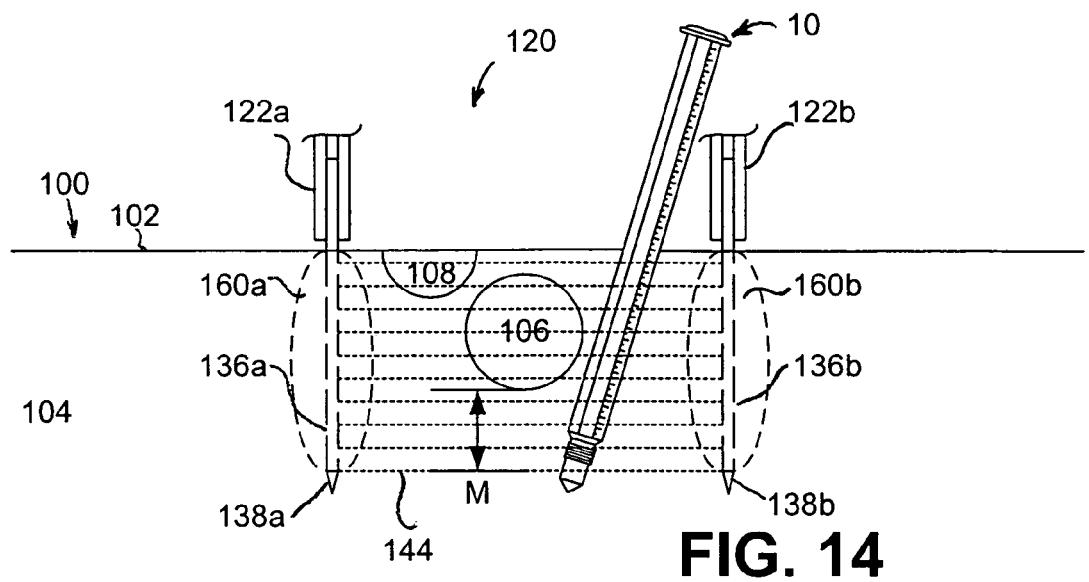
FIG. 14 is a cross-sectional side view of a distal end portion of another embodiment of an electrosurgical device used with the temperature indicating device of FIG. 1.

In other embodiments, as shown in FIG. 14, electrosurgical device 120 may comprises a bipolar device having electrodes 138a, 138b comprising two needles with each having at least one fluid outlet opening 136a, 136b through which fluid 116 and radio frequency energy may be delivered into tissue 100. Zones 160a, 160b of tissue 100 comprise tissue 100 which has been infiltrated by fluid 116.

Figure 15:
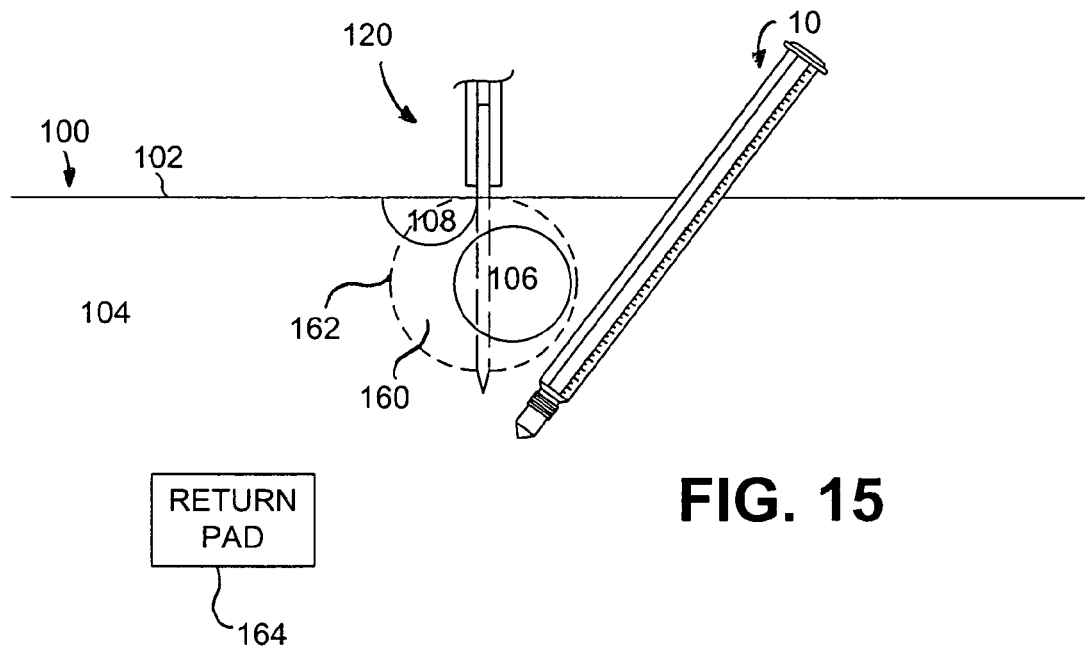
FIG. 15 is a cross-sectional side view of a distal end portion of another embodiment of an electrosurgical device used with the temperature indicating device of FIG. 1.

In still other embodiments, as shown in FIG. 15, electrosurgical device 120 may comprise a monopolar device. More specifically, as shown in FIG. 15, electrosurgical device comprises a single electrode 138 comprising a needle having at least one fluid outlet opening 136 through which fluid 116 and radio frequency energy may be delivered into tissue 100. As shown, electrode 138 has been inserted into and through abnormal tissue 106, and fluid 116 has completely infiltrated abnormal tissue as shown by fluid infiltration zone 160 which is defined by fluid infiltration border 162.

With use of a monopolar device 120, the first electrode, often referred to as the active electrode, comprises electrode 138 of the electrosurgical device 120 while a second electrode, often referred to as the indifferent or return electrode, comprises a ground pad dispersive electrode 164 located on the patient and coupled to energy source 92, typically on the back or other suitable anatomical location. An electrical circuit is formed between electrode 138 and ground pad dispersive electrode 164 with electrical current flowing from electrode 138 through the patient to ground pad dispersive electrode 164 in a manner known in the art.

In addition to the monopolar device shown in FIG. 15, it should be understood that the bipolar device shown in FIGS. 10 and 11 can be also used as a monopolar device with the elimination of one of the electrodes thereof.

From the specification, it should be clear that any use of the terms "distal" and "proximal" are made in reference from the user of the device 10, and not the patient. Furthermore, it should also be understood that such terms are used to distinguish the various portions of device 10 relative to one another, and as device 10 will preferably be used as shown in the figures. Consequently, these terms should not be understood to be otherwise limiting since device 10 may obviously be disposed in many different orientations when in actual use.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents.

Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes, to the extent they are consistent.

We claim:

1. A method of treating tissue of a living human body during a surgical procedure comprising:
   providing tissue, the tissue comprising normal tissue and abnormal tissue;
   inserting at least one temperature indicating device into the tissue, the temperature indicating device comprising:
      a movable indicator to provide an indication of when a trigger temperature has been attained by the normal tissue; and
      a trigger mechanism to trigger an activation of the indicator when heated to the trigger temperature;
   heating a targeted section of the tissue sufficiently to ablate at least a portion of the abnormal tissue; and
   transferring heat from the heated tissue to the trigger mechanism, the heat sufficient to heat the trigger mechanism to the trigger temperature and trigger the activation of the indicator,
   wherein the indicator comprises a rod which provides an indication of when the trigger temperature has been attained by movement thereof,
   wherein the temperature indicating device further comprises a housing, the housing having a barrel portion, the barrel portion including at least one planar exterior surface extending longitudinally along the length thereof, the planar surface including a series of markings thereon corresponding to a length measurement; and the indicator rod moves relative to the housing from a retracted position to an extended position.

2. The method of claim 1 wherein:
the trigger mechanism comprises a fusible link between the indicator rod and the housing.

3. The method of claim 2 wherein:
the trigger mechanism comprises fusible material which provides the fusible link between the indicator rod and the housing.

4. The method of claim 3 wherein:
the fusible material consists essentially of a composition biocompatible with the human body.

5. The method of claim 1 wherein:
the trigger mechanism to trigger the activation of the indicator when heated to the trigger temperature comprises a material configured to physically weaken when heated to the trigger temperature.

6. The method of claim 1 wherein:
the trigger mechanism to trigger the activation of the indicator when heated to the trigger temperature comprises a structure configured to deform when heated to the trigger temperature.

7. The method of claim 1 wherein:
heating the tissue is provided by resistive heating, and the tissue is heated to a temperature of 45° C. to 60° C.

8. The method of claim 7 wherein:
resistive heating is provided by the resistance of the tissue to a passage of electrical current provided from an electrosurgical instrument, the electrosurgical instrument to treat tissue by moving along a surface of the tissue in a presence of radio frequency energy and a fluid provided by simultaneously from a distal portion of the instrument.

9. The method of claim 1 further comprising:
using a body imaging device to locate at least a portion of the abnormal tissue.

10. The method of claim 9 wherein:
using a body imaging device to locate at least a portion of the abnormal tissue is performed before inserting at least one temperature indicating device into the tissue.

11. The method of claim 1 further comprising:
using a body imaging device to locate at least a portion of the temperature indicating device.

12. The method of claim 11 wherein:
using a body imaging device to locate at least a portion of the temperature indicating device is performed during inserting at least one temperature indicating device into the tissue.

13. The method of claim 1 further comprising:
using a distance between the temperature indicating device and the abnormal tissue as a treatment margin.

14. The method of claim 13 further comprising:
heating the tissue sufficiently to ablate at least a portion of the margin.

15. The method of claim 1 wherein:
inserting at least one temperature indicating device into the tissue further comprises inserting a plurality of temperature indicating devices into the tissue.

16. The method of claim 15 wherein:
inserting a plurality of temperature indicating devices into the tissue further comprises inserting the plurality of temperature indicating devices into the normal tissue at least partially around the abnormal tissue.

\* \* \* \* \*